United States Patent [19]

Tomimatsu et al.

[11] Patent Number: 4,482,706

[45] Date of Patent: Nov. 13, 1984

[54] STEROID SAPONINS

[75] Inventors: Toshiaki Tomimatsu; Kotaro Murakami, both of Tokushima, Japan

[73] Assignee: Tokiwa Yakuhin Kogyo Kabushiki Kaisha, Osaka, Japan

[21] Appl. No.: 491,964

[22] PCT Filed: Sep. 24, 1982

[86] PCT No.: PCT/JP82/00384

§ 371 Date: Apr. 20, 1983

§ 102(e) Date: Apr. 20, 1983

[87] PCT Pub. No.: WO83/01065

PCT Pub. Date: Mar. 31, 1983

[30] Foreign Application Priority Data

Sep. 25, 1981 [JP] Japan .................................. 56-152488

[51] Int. Cl.³ ............................................. C07J 17/00

[52] U.S. Cl. ......................................... 536/6.1; 536/5; 536/181; 260/397.4

[58] Field of Search ........................... 536/5, 6.1, 18.1

[56] References Cited

U.S. PATENT DOCUMENTS

| | | | |
|---|---|---|---|
| 4,101,652 | 7/1978 | Bonati | 536/5 |
| 4,265,886 | 5/1981 | Pegel | 536/5 |
| 4,320,225 | 3/1982 | Hashimoto et al. | 536/18.1 |

*Primary Examiner*—Johnnie R. Brown
*Assistant Examiner*—Elli Peselev

[57] ABSTRACT

Novel steroid saponin compounds (XR-1) and (XR-2) are extracted from *Solanam aculeatissimum*, a plant belonging to the Solanum genus, and 16-dehydropregnenolone is obtained by hydrolyzing the said compounds, subjecting the hydrolyzed product to Marker's degradation, and treating the obtained product with aqueous alkali.

2 Claims, No Drawings

STEROID SAPONINS

DESCRIPTION

FIELD OF THE INVENTION

The present invention relates to novel steroid saponins obtained from plants belonging to Solanaceae, extraction of the said steroid saponins and process for preparing 16-dehydropregnenolone or its ester from the said steroid saponins.

BACKGROUND OF THE INVENTION

Said 16-dehydropregnenolone is a compound having the following formula:

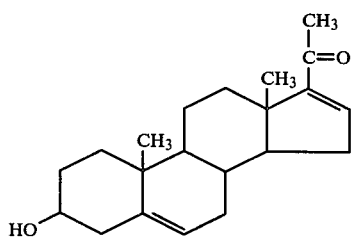

and is useful as an intermediate for preparing various sexual hormones, corticoids, oral contraceptive drugs etc. It is known that 16-dehydropregnenolone is prepared from diosgenin which is contained mainly in plants of the genus Dioscorea. However, *Dioscorea tokoro* and some other analogous species, which are the diosgenin containing plants growing in Japan, are not satisfactory source of supply for diosgenin because their rhizomes are poor and contents of diosgenin are less than only 1%. The chief source of diosgenin at the present time is *Dioscorea composita* (*barbasco*) which is a naturally growing species in Mexico. However, this species is not reliable source because it is a wild plant. It has therefore been felt anxious about deficiency of diosgenin source and found necessary to develop a novel preparative method for 16-dehydropregnenolone from other source.

DISCLOSURE OF THE INVENTION

As a result of an extensive study searching for steroid saponin containing plants which may be a source for the preparation of 16-dehydropregnenolone carried out by the present inventors, it has now been discovered that Solanum species belonging to Solanaceae, typically *Solanum aculeatissimum* Jacq., contains steroid saponin compounds represented by formulae (XR-1) and (XR-2) described later in a high content, that these compounds can be successfully extracted, and that 16-dehydropregnenolone can be prepared using these compounds as starting materials.

According to the invention, there are provided (1) a compound represented by the following formula (XR-1):

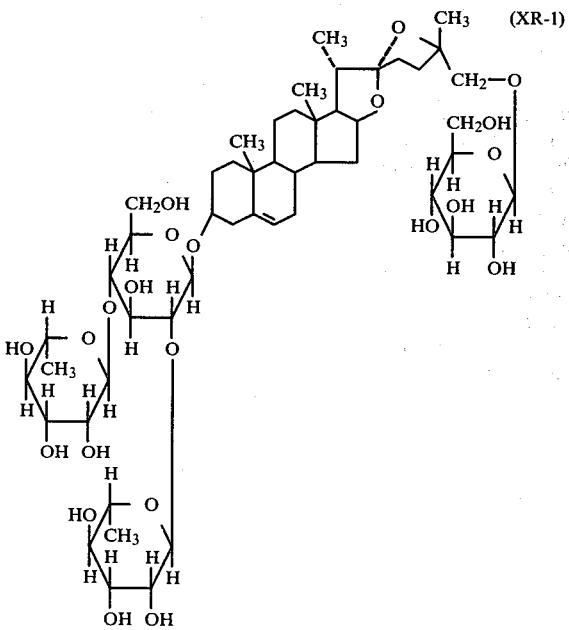

(2) a compound represented by the following formula (XR-2):

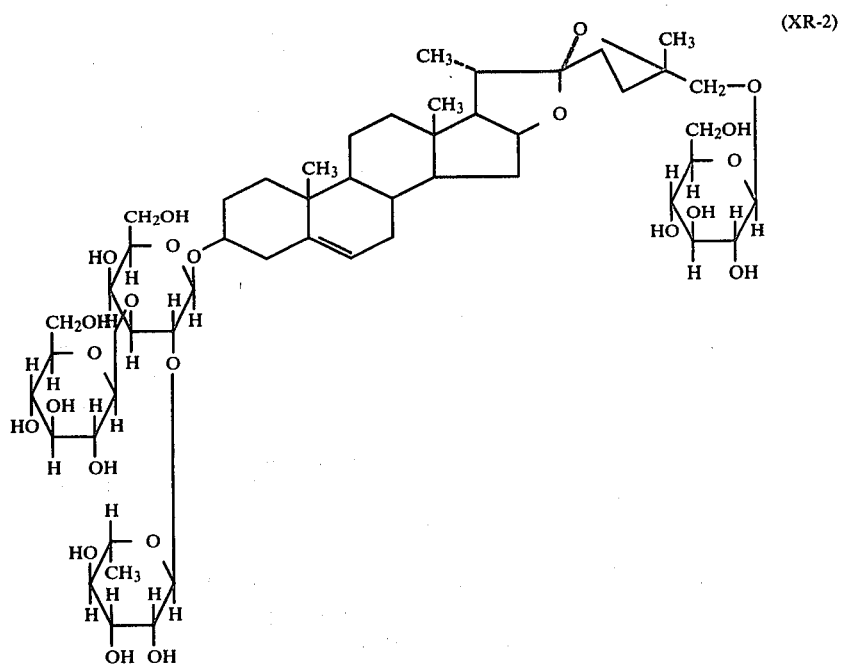

(XR-2)

(3) a process for extracting the compounds (XR-1) and (XR-2) which comprises extracting a plant belonging to the Solanum genus and containing the compounds (XR-1) and (XR-2) with water or an organic solvent and separating the compounds (XR-1) and (XR-2) contained in the extract, and (4) a process for preparing 16-dehydropregnenolone or lower aliphatic acid ester thereof which comprises hydrolyzing the compound (XR-1) or (XR-2), subjecting the obtained product to Marker's degradation and treating the obtained product with water, a lower alcohol or a lower aliphatic acid.

In the process for extracting the compounds (XR-1) and (XR-2), it is preferable to use water or a hydrophilic organic solvent, especially water, a lower alcohol (such as for example, methanol, ethanol, propanol etc.) or a mixture thereof. The compounds (XR-1) and (XR-2) can be obtained in an isolated state, or as a mixture of these two compounds, by treating the said extract, or extract (organic phase) obtained by extracting the concentrate of the said extract with other solvent (for example, a mixture of water: butanol=1:1), with the conventional means such as concentration, crystallization, recrystallization, chromatography, solvent-partition etc. Since both the compounds (XR-1) and (XR-2) can be used for preparing 16-dehydropregnenolone in the same way, it is not necessary to separate these two compounds and it is more preferable to use as a mixture of the two compounds.

The compounds (XR-1) and (XR-2) have the following physical properties when they are isolated.

XR-1
colorless needles
m.p.: 196°–204° C.
angle of rotation: $[\alpha]_D^{27} = -28.4°$ (c=1.02, pyridine)
FD-MS (m/Z): 1069
IR $\nu_{max}^{KBr}$ (cm$^{-1}$): 3400
CMR (d5-py.)
$\delta$(ppm)=15.03, 16.11, 18.25, 18.40, 19.33, 21.04, 24.31, 30.06, 31.63, 32.16, 32.16, 33.09, 33.77, 37.04, 37.48, 38.56, 38.85, 39.83, 40.46, 50.22, 56.42, 61.35, 62.42, 62.62, 69.25, 70.28, 71.55, 72.18, 72.18, 72.48, 72.48, 73.60, 73.89, 75.11, 76.28, 77.21, 77.75, 78.10, 78.10, 78.10, 78.10, 78.97, 80.87, 83.75, 100.15, 101.76, 102.69, 105.08, 120.11, 121.68, 140.70

XR-2
angle of rotation: $[\alpha]_D^{28} = -57.7°$ C. [c=0.75, methanol:water (1:1 V/V)]
FD-MS (m/z): 1085, 1069
IR $\nu_{max}^{KBr}$ (cm$^{-1}$): 3400
CMR (d5-py.)
$\delta$(ppm)=15.08, 16.15, 18.45, 19.38, 21.13, 24.31, 30.11, 31.68, 32.16, 32.16, 33.14, 33.82, 37.09, 37.48, 38.61, 38.61, 39.83, 40.51, 50.32, 56.47, 61.69, 62.23, 62.42, 62.67, 69.25, 69.94, 71.60, 71.60, 72.18, 72.57, 73.94, 74.72, 74.91, 75.16, 76.04, 77.26, 77.70, 78.14, 78.14, 78.14, 78.14, 80.92, 83.80, 84.97, 100.44, 101.95, 105.13, 105.47, 120.16, 121.57, 140.85

In the process for preparing 16-dehydropregnenolone, the hydrolysis of the compound (XR-1) or (XR-2) is effected by treating the compound with mineral acid such as hydrochloric acid, sulfuric acid etc. in water, lower alcohol (methanol, ethanol, isopropanol etc.) or a mixture thereof. It is advisable to use the mineral acid in an amount exceeding the equimolar amount. The reaction is usually carried out by heating at a temperature around 70° C. for 2 to 5 hours. By this hydrolysis are produced nuatigenin of the formula:

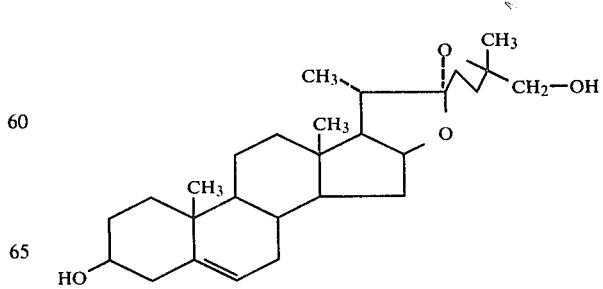

and isonuatigenin of the formula:

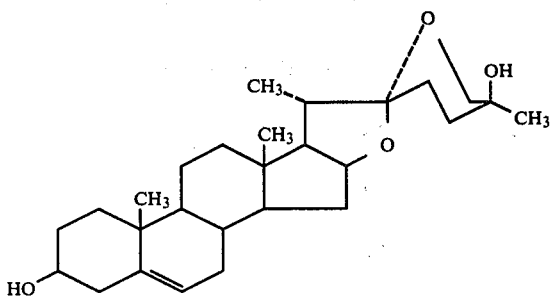

which is a secondary product. These compounds may be used in following steps as crude products, though they may be obtained in a pure state, for example, by subjecting the hydrolyzate to chromatography on silica gel column and eluting with a solvent such as a mixture of chloroform:methanol (100:100).

Marker's degradation involves acetolysis and chromic acid oxidation (for example, Fieser & Fieser, "Steroids" page 549, 1959).

The acetolysis is effected by reacting the above compounds with acetylating agent (acetic anhydride, acetyl chloride, 2,3-diacetoxypyridine etc.). This reaction may be carried out, for example, in two steps in which the said compounds are firstly reacted with an excess of the said acetylating agent in a solvent (acetic acid, pyridine, methanol, ethanol, isopropanol) at around 0°–150° C. (preferably room temperature to 110° C.) for 2–15 hours, and secondly reacted with acetic anhydride in a sealed tube at around 195° C. for 18 hours. In this case, it is presumed that a mixture of the following two compounds is produced by the first step treatment.

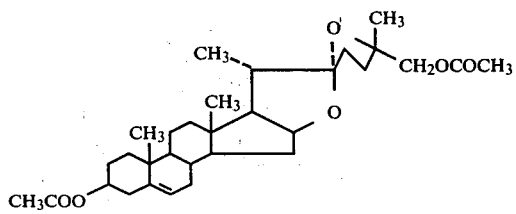

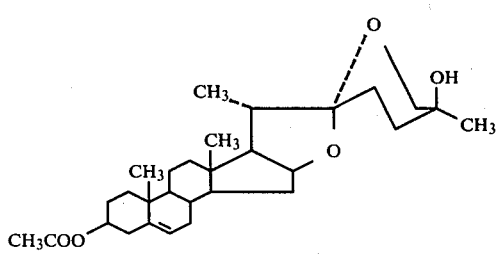

These products in the first step may be used in the second step treatment after purifying, for example, by chromatography on alumina column (using a mixture of cyclohexane:benzene=7:3 as an eluent). The reaction may be accelerated by an acid (for example, toluenesulfonic acid) or a Lewis acid (for example, aluminum chloride). There may be used an organic acid (for example, octanoic acid) as a solvent. It is presumed that the following compound is produced in this reaction.

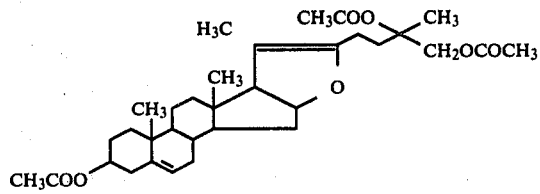

The chromic acid oxidation is effected by reacting the above acetolysis product with chromic anhydride. It is advisable to use chromic anhydride in an amount around three times the equimolar amount. As to the reaction conditions, a standing at around room temperature to 22° C. for about an hour is sufficient. Reaction product may be separated, for example, by adding water to the reaction mixture and extracting the resulting mixture with ether. It is presumed that the following compound is produced in this chromic acid oxidation.

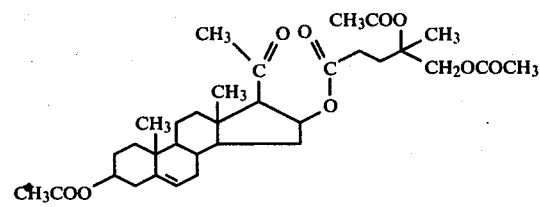

The above compound gives on treatment with water or a lower alcohol (for example, tert-butanol) in the presence of a base (for example, sodium hydroxide, potassium hydroxide) 16-dehydropregnenolone and on treatment with a lower aliphatic acid (for example, acetic acid) an aliphatic acid ester of 16-dehydropregnenolone. The treatment with water or the lower alcohol is usually carried out at 30° C. for about 3 hours. The treatment with the aliphatic acid is usually carried out under reflux. Reaction product may be isolated by extraction with ether and chromatography on alumina column (using a mixture of cyclohexane:benzene=1:4 as an eluent).

PREFERRED EMBODIMENTS OF THE INVENTION

The invention will now be further illustrated by means of the following examples.

EXAMPLE 1

Extraction of the Compounds (XR-1) and (XR-2)

Either 725 g of undried root or 290 g of dried root from *Solanum aculeatissimum* is extracted with methanol, denatured alcohol, ethanol or water. The liquid phase is concentrated under reduced pressure to give about 70 g of extract, from which fat is removed as required. The extract containing the compounds (XR-1) and (XR-2), thus obtained, may be used for preparation of 16-dehydropregnenolone without further treatment.

EXAMPLE 2

Preparation of 16-Dehydropregnenolone from a Mixture of the Compounds (XR-1) and (XR-2)

(a) Hydrolysis

To the extract obtained in Example 1 is added 700 ml of 2N-methanolic hydrochloric acid. The obtained mixture is heated under reflux for 2 hours. After cooling, the mixture is neutralized with 5%—methanolic solution of sodium hydroxide or potassium hydroxide and evaporated under reduced pressure. The residue is used in the following steps without further treatment. Alternatively, the residue is treated with methanol to dissolve organic substances. Insoluble salts are removed by filtration and methanol is removed by distillation from the filtrate giving residue (about 24 g).

(b) Marker's degradation

The whole quantity of the residue obtained in (a) is dissolved in a small amount of pyridine and acetylated by adding about 230 ml of acetic anhydride and warming or standing overnight. The acetate, which is obtained on removing the solvent by distillation, is used with or without purification by column chromatography on alumina. The acetate is dissolved in 32 g of acetic anhydride. The obtained solution is heated at 195° C. for 18 hours in a sealed glass tube. After cooling, the seal is broken and 8 ml of water is added to the solution. A solution of 6.7 g of sodium acetate in 200 ml of glacial acetic acid is added to the warmed solution, which was then cooled to 15° C. A solution of 11 g of chromium trioxide in 43 ml of glacial acetic acid is added to the solution with stirring over a period of 15 minutes and allowed to react, while the temperature is kept constant at 15° C. The mixture is left to stand for an hour keeping the temperature at 22° C. and partitioned between water and ether (or ethyl acetate or other suitable solvent). The upper phase is concentrated to give a syrupy substance.

(c) Treatment with an aqueous alkali solution

To the syrupy substance are added 500 ml of tert-butanol and several drops—several mililliters of a solution of 1 g of potassium hydroxide (or 0.7 g of sodium hydroxide) in 1.2 ml of water. The obtained mixture is stirred at 30° C. for 3 hours. Then the mixture is partitioned between water and ether (or ethyl acetate). The upper phase is dried and solvent is removed by distillation from the upper phase. The residue is subjected to chromatography over alumina column eluting with cyclohexane:benzene (2:8 V/V) or other suitable solvent to give about 10 g of 16-dehydropregnenolone (about 41.6% on the basis of acidhydrolyzate).

The obtained 16-dehydropregnenolone has the following physical properties:

colorless plates,

Rf: 0.41 (silica gel, chloroform:methanol=55:3 V/V)

m.p.: 209°–212° c.

angle of rotation: $[\alpha]_D^{22} = -36°$ (c=2.0, chloroform)

ultraviolet absorption: $\lambda_{max}=239$ nm (log$\epsilon$=3.91)

When the syrupy substance is treated with boiling acetic acid in place of the aqueous alkali solution, 16-dehydropregnenolone acetate is obtained.

We claim:

1. A compound represented by the following formula (XR-1):

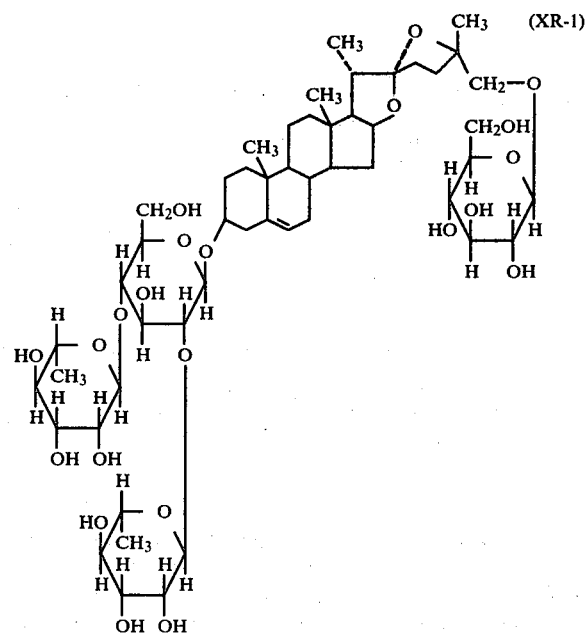

2. A compound represented by the following formula (XR-2):

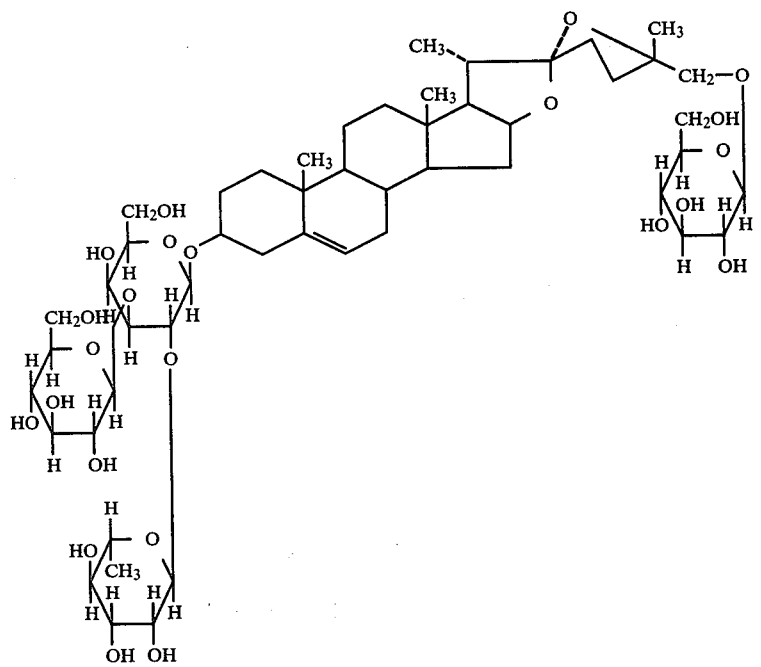
(XR-2)